United States Patent [19]

Borretzen et al.

[11] Patent Number: 5,149,820
[45] Date of Patent: Sep. 22, 1992

[54] DEUTERATED COMPOUNDS

[75] Inventors: Bernt Borretzen; Rolf O. Larsen, both of Porsgrunn; Erik O. Pettersen; John M. Dornish, both of Oslo; Reider Oftebro, Hvalstad, all of Norway

[73] Assignee: Norsk Hydro A.S., Oslo, Norway

[21] Appl. No.: 396,218

[22] Filed: Aug. 21, 1989

Related U.S. Application Data

[62] Division of Ser. No. 24,783, Mar. 11, 1987, Pat. No. 4,874,780.

[51] Int. Cl.$^5$ ............... C07D 263/04; C07D 339/08
[52] U.S. Cl. ...................... 548/215; 549/14; 549/39
[58] Field of Search ............ 548/215, 235, 240, 247, 548/237, 239; 549/13, 35, 39, 14

[56] References Cited

U.S. PATENT DOCUMENTS 4,906,277  3/1990  Oda et al. .................. 548/240

FOREIGN PATENT DOCUMENTS 0041674  12/1981  European Pat. Off. .
0220573   5/1987  European Pat. Off. .
1263975  11/1986  Japan .
0010082   1/1987  Japan .
3227576   9/1988  Japan .

OTHER PUBLICATIONS

Borretzen et al., "Anticancer compositions containing vitamin-C and deuterated derivatives" CA 112 48786u (1990).

Borretzen et al., "Preparation of deuterated aromatic aldehydes as anticancer compounds" CA 111 109028b (1989).

*Primary Examiner*—C. Warren Ivy
*Assistant Examiner*—Amelia A. Owens
*Attorney, Agent, or Firm*—Wenderoth, Lind & Ponack

[57] ABSTRACT

Deuterated aromatic aldehydes of the formula:

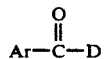

where Ar is substituted phenyl, and derivatives thereof represented by the formula:

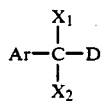

where Ar is substituted or unsubstituted phenyl, and $X_1$ and $X_2$ are substituted hetero atoms or together with the carbon to which they are attached form a heterocycle. These compounds are useful as anticancer and analgesic agents.

1 Claim, No Drawings

DEUTERATED COMPOUNDS

This application is a division of Ser. No. 07/024,783 filed Mar. 11, 1987, now U.S. Pat. No. 4,874,780.

BACKGROUND OF THE INVENTION

The present invention relates to new anticancer compounds. Such compounds are made from aromatic aldehydes and derivatives thereof, where certain H-atoms have been replaced by deuterium atoms.

Anticancer drugs on the basis of aromatic aldehydes and derivatives thereof are known according to the present state of the art.

Certain aromatic aldehydes and derivatives of aldehydes have proven effective in treatment of various cancers of carcinoma type, both in animal systems and in human patients. This has been reported in the literature by Kochi et al., Cancer Treat. Rep., 64: 21-23, (1980); Kochi et al., 13th International Cancer Conference, Seattle, WA, USA, (1982); Kochi et al., Cancer Treat. Rep., 69: 533-537, (1985) and Pettersen et al., Anticancer Res., 6: 147-152 (1986). GB patent 1.582.666, DE patent 27 10 327 and EP-A 0 148 094 also describe the effects of such aldehydes.

Due to instability and low activity of these substances on cancer cells it is necessary to administer relatively high doses frequently. It has been reported that treatment of patients must be conducted continuously for at least several months, and in some cases for years, to cure the patient (Kochi 80, 85).

SUMMARY OF THE INVENTION

According to the present invention, we have found new and improved anticancer compounds showing greater biological activity where the above drawbacks are reduced.

These new compounds are deuterated aromatic aldehydes which can be represented by formula (I):

(I)

where Ar is substituted phenyl which may be fully or partly deuterated, and derivatives of deuterated aromatic aldehydes which can be represented by formula (II):

(II)

where Ar is substituted or unsubstituted phenyl which can also be at least partly deuterated, and where $X_1$ and $X_2$ are substituted hetero atoms, or $X_1$ and $X_2$, together with the carbon to which they are attached, form a heterocycle, for example thus forming cyclic acetals, thioacetals, thianes, oxazolidines, etc.

The present invention also provides a process for preparing deuterated compounds, anticancer compositions containing deuterated compounds, and a method of treating a patient afflicted with cancer.

DETAILED DESCRIPTION OF THE INVENTION

With regard to the new compounds themselves, in formula (I) and (II) above, D represents a deuterium atom.

In formula (I), Ar is a substituted phenyl group which can be fully or partly deuterated. The substitutents for the phenyl group are exemplified by alkyl of 1-5 carbon atoms, e.g. methyl, ethyl, n-propyl and i-propyl, cycloalkyl of 3-6 carbon atoms, e.g. cyclopropyl and cyclohexyl, halogen, e.g. chlorine and bromine, nitro, amino, monoalkylamino of 1-5 carbon atoms in the alkyl group, e.g. monomethylamino, and dialkylamino of 1-5 carbon atoms in each alkyl group, e.g. dimethylamino. Preferably, the substituted phenyl group contains 1-3 substitutents.

Ar in formula (I) can optionally be at least partly deuterated, i.e. one or more of the hydrogen atoms in the Ar group, including any substitutents thereon, can be replaced by deuterium atoms.

In formula (II), Ar is substituted or unsubstituted phenyl. The substituents for the phenyl group are exemplified as above for the compounds of formula (I). Preferably, when the phenyl group does contain substitutents, there are 1-3 substituents.

The Ar group in formula (II) can optionally be at least partly deuterated, as defined above in connection with formula (I).

As indicated above, $X_1$ and $X_2$ can be substituted hetero atoms. Examples of the hetero atoms are sulfur, oxygen and nitrogen. The substituents include hydrogen, alkyl of 1-5 carbon atoms (exemplified as above), cycloalkyl of 3-6 carbon atoms (exemplified as above), and phenyl. Thus, for example, $X_1$ and $X_2$ can be hydroxy, mercapto, amino, methoxy, cyclopropyloxy, phenoxy, methylthio, cyclopropylthio, phenylthio, monomethylamino, dimethylamino, monocyclopropylamino or monophenylamino.

Alternatively, the $X_1$ and $X_2$ can form, together with the carbon atoms to which they are attached, a heterocycle, thus forming, as the compound of formula (II), for example, a cyclic acetal, thioacetal, thiane or oxazolodine.

In a preferred embodiment of this invention, $X_1$ and $X_2$ in formula (II) are linked together to form cyclic acetals with polyhydric alcohols such as sugars and sugar derivatives, such as D-glucose, L-ascorbic acid (and salts), etc.

The present invention also includes salts of the foregoing compounds, such as pharmaceutically acceptable salts, for example the alkali metal and alkaline earth metal salts.

The present invention also relates to a process for preparation of highly deuterated products of aromatic aldehydes, and the products obtained thereby, where a high degree of deuteration has been achieved.

To date a number of methods exist for the small scale preparation of deuterated aromatic aldehydes. However, these processes suffer from various disadvantages such as low yield, many reaction steps, and too low a degree of deuteration in the final product.

Thus, the present invention provides a process for preparing deuterated aromatic aldehydes, which comprises reducing an aromatic acid halide, such as an aromatic acid chloride, with deuterium gas in a highly deuterated solvent. The reaction is preferably carried out in the presence of a transition metal catalyst such as Pt, Pd, etc., and more preferably with Pd on solid support such as BaSO$_4$.

These reaction conditions correspond to the well known Rosenmund-reaction for preparing pratio-aldehydes from the corresponding acid chlorides with H$_2$-gas (Rosenmund, Chem. Berichte, 51: 585, (1918)).

However, in the process of the present invention the reduction of the acid chloride with D$_2$-gas is carried out in a highly deuterated aromatic solvent, i.e. in which at least 90% of the protons in the solvent molecules have been replaced (substituted) by deuterium atoms. The reduction is preferably carried out in highly deuterated benzene, toluene, ethylbenzene or xylene. The deuterated solvents can be prepared by conventional techniques well known in the art via H/D-exchange reactions.

The weight ratio between the aromatic acid halide and the highly deuterated solvent is preferably 1:3 to 1:10. The D$_2$-gas is preferably introduced into the reaction mixture at a rate of 10-20 liters per hour, and the reaction is preferably conducted at a temperature of 50°-2000°C., more preferably at the reflux temperature of the reaction mixture.

The process as set forth above results in production of compounds of formula (I). These compounds can be converted to compounds of formula (II), by a process which is analogous to the well known process for the preparation of cyclic derivatives of aromatic aldehydes. In general, this process involves reacting the aldehyde or a lower acetal of the aldehyde with a di- or polyhydric alcohol in the presence of an acidic catalyst. The reaction is preferably carried out in a dipolar solvent such as dimethyl formamide, dimethyl sulfoxide, dimethyl acetamide and the like. Examples 3 and 4 describe the preparation of the new compounds of formula (II) by such an analogous process, in which the high degree of deuteration in the aldehyde group of the formula (I) starting material is retained during the reaction.

Since the anticancer effects of the deuteroaldehydes and the corresponding derivatives are directly related to the —C—D group in formulae (I) and (II) (hereinafter "the aldehyde group"), and thus the aldehyde group is responsible for the anticancer effect, it should be understood that the present invention is not restricted to specific derivatives of deuterated aromatic aldehydes, other than as broadly indicated above, and that anticancer compositions in which the aromatic deuteroaldehydes or derivatives of aromatic deuteroaldehydes are the active ingredient will be much more potent than the corresponding aromatic aldehydes and derivatives.

Anticancer compositions based on aromatic deuteroaldehydes or derivatives thereof will thus have a much broader applicability than those based on the corresponding non-deuterated aldehydes and derivatives.

The products prepared by the deuteration process of the present invention, i.e. the process of reducing the aromatic acid halide to the deuterated aromatic aldehyde, will contain both the non-deuterated aromatic aldehyde and the desired deuterated aromatic aldehyde as final products, in those cases where deuteration is incomplete. In terms of the utility of these compositions, for the treatment of patients afflicted with cancer, these partially deuterated products can be used, but the best results are attained with completely deuterated products, i.e. where substantially all of the aromatic aldehyde final product is in the form of deuterated aromatic aldehyde corresponding to formula (I).

A particularly useful aldehyde for treatment of patients with cancer is deuterobenzaldehyde, and derivatives of deuterobenzaldehyde.

Thus, according to the present invention, there is provided a very efficient process for preparing highly deuterated aromatic aldehydes in which a very high degree of deuteration in the aldehyde group has been achieved.

The compositions of the present invention for treating patients afflicted with cancer contain (A) a deuterated aromatic aldehyde which can be represented by formula (III):

(III)

where Ar is substituted or unsubstituted phenyl which can be at least partly deuterated, and derivatives of deuterated aromatic aldehydes which can be represented by formula (II):

(II)

where Ar is substituted or unsubstituted phenyl which can be at least partly deuterated, and where X$_1$ and X$_2$ are substituted hetero atoms, or X$_1$ and X$_2$, together with the carbon to which they are attached, form a heterocycle, and (B) a pharmaceutically acceptable carrier.

Formula (III) differs from formula (I) only in that in the former Ar can be unsubstituted phenyl, i.e. formula (III) encompasses deuterobenzaldehyde.

The products and process of the present invention will be further explained by reference to the following examples, but the present invention is not restricted thereby.

EXAMPLE 1

Method for preparing deuterobenzaldehyde

To 260 ml dry toluene-d$_8$ (degree of deuteration: 99.5%) in which was suspended 5.2 g of 5% Pd on BaSO$_4$ catalyst, was added 54.8 g of freshly distilled benzoylchloride. Eventually, a regulator such as "S-quinoline" (Rosenmund, Chem. Ber. (1918)) can be added to modify the activity of the catalyst.

Via a gas-inlet tube, D$_2$-gas containing 99.7 atom % D was introduced with rapid stirring of the reaction mixture. The reduction reaction was conducted at the reflux temperature of the reaction mixture. The reaction can be followed by GLC of the reaction mixture or by measuring the evolved DCl which is formed during the reaction. After approximately 20 hr all the acid chloride had reacted and the D$_2$-gas supply is removed.

The deuterated benzaldehyde can be worked up from the reaction mixture in a conventional manner by distillation of the reaction mixture.

However, a much easier and less time consuming way to obtain a pure product is by complexing out the formed deuterobenzaldehyde by rapid stirring of the aldehyde-containing toluene solution with a saturated solution of sodium bisulfite in heavy water. Due to slow H/D-exchange of the deuterium atom of the aldehyde group in the sulfite-complex in ordinary water, it is also preferred to make the saturated sodium bisulfite solution in heavy water, at least if a highly deuterated aldehyde is desired.

The aldehyde can then be regenerated from the complex by reacting the complex with a basic water solution.

Thus, after filtering off the catalyst in the reaction mixture, the resulting clear toluene solution was mixed with approximately 250 ml of a saturated solution of sodium bisulfite in $D_2O$ and stirred rapidly under an inert atmosphere for approximately 10 hr.

The resulting sodium sulfite-complex of deuterated benzaldehyde was then filtered, washed several times with ether and dried.

The deuterated solvent used in the reaction can easily be dried and reused in a following batch.

Deuterobenzaldehyde-$d_1$ is generated from the resulting pure sodium sulfite complex by adding 600 ml of 5% sodium carbonate solution with rapid stirring at room temperature.

The deuterobenzaldehyde-$d_1$ is then extracted several times with 250 ml diethyl ether.

The ether extracts are then combined, dried and the diethyl ether is removed under vacuum.

The residual deuterobenzaldehyde was then distilled under reduced pressure and gave 24 g of chemically pure deuterobenzaldehyde-$d_1$, Bp 74° C., (22 mm Hg). $n_D = 1.5436$ Degree of deuteration (by NMR)=99.5% D.

COMPARATIVE EXAMPLE 1

To 260 ml ordinary toluene (Merck, p.a.) in which was suspended 5.2 g of catalyst (5% Pd on $BaSO_4$), was added 54.8 g of freshly distilled benzoylchloride.

Via the same gas-inlet tube as described in Example 1 $D_2$-gas was introduced at a rate of ~15 l/hr.

After 20 hr reaction time the reaction mixture was worked up as described in Example 1.

Thus there was obtained 23 g of chemically pure deuterobenzaldehyde-$d_1$.

Degree of deuteration: 66% D.

Thus this example shows that in order to obtain a deuteroaldehyde with a high degree of deuteration, it is very essential that the solvent used in the reduction of the acid chloride is highly deuterated, in order to prevent dilution of the $D_2$-gas by exchanging the protons in the aromatic solvents.

EXAMPLE 2

Method for preparing deuterobenzaldehyde

The preparation was conducted according to the procedure described in Example 1, but with deuterated ethyl benzene as solvent.

Thus to 300 ml deuterated ethyl benzene (degree of deuteration: 99.4%), in which was suspended 7.6 g of 5% Pd on $BaSO_4$ catalyst, was added 54.7 g of freshly distilled benzoylchloride.

Via a gas inlet tube, $D_2$-gas was bubbled through the reaction mixture with rapid stirring. The $D_2$-gas was introduced at a rate of approximately 15 l per hour.

Again the reduction was carried out at the reflux temperature of the reaction mixture, which was 140°-145°C. After 4-5 hr reaction time all the benzoylchloride had been consumed as shown by GLC-analysis, and the $D_2$-supply was removed, and the reaction mixture cooled to room temperature.

The deuterobenzaldehyde was worked up from the reaction mixture as described in Example 1, and gave 23 g of pure deuterobenzaldehyde-$d_1$.

Degree of deuteration: 99.4 atom % D.

EXAMPLE 3

Method for preparing deutero 4,6-0-benzylidene-$d_1$-glucose (BG-$d_1$)

56 g of deuterobenzaldehyde as prepared in Example 1 and 2, are reacted with 50 g of methanol and 61 g of trimethylorthoformate in the presence of 0.8 g hydrochloric acid, while stirring the reaction mixture.

After 0.5 hr reaction time at 50° C., the low boiling components of the reaction mixture were removed under vacuum, followed by distilling off the formed deuterated benzaldehyde-dimethylacetate (α,α-dimethoxy-α-$d_1$-toluene).

After redistilling 75 g of pure α,α-dimethoxy-α-$d_1$-toluene was obtained. Bp 195° C.

Degree of deuteration (by NMR)=99.5% D.

20 g of this product was added to a mixture of 23.4 g D-glucono-δ-lactone in 100 ml dimethylformamide (DMF) followed by 0.7 g of p-toluene sulfonic acid. The reaction mixture was refluxed at 60°-70° C. under a slight vacuum while continuously removing the formed methanol. After all the methanol has been driven off, the DMF was removed under vacuum. The oily residue, which consists mainly of deutero 4,6-benzylidene-D-glucono-δ-lactone can be further reduced to the corresponding D-glucose-derivative in the following way. Thus the oily residue was diluted with 250 ml methanol followed by 300 ml of distilled water and subsequently cooled to 0°-5° C.

To this mixture was added alternately 4.8 g of sodium borohydride in 150 ml distilled water and 4.5 g concentrated sulfuric acid in 150 ml water while maintaining the pH of the suspension between 5 and 8. After 1 hr reaction time the pH of the solution was adjusted to pH 9, and concentrated under reduced pressure to approximately 400 ml total.

The product can be worked up in a conventional manner as by absorbing the product on Amberlite. Thus by adding 500 g of Amberlite XAD-2 to the water solution (3 l), stirring for 30 minutes, filtering and desorbing the product with methanol, removing methanol under reduced pressure, a light brown oil is obtained, 20 g, which crystallizes in the cold.

By stirring this oil with 20 ml ice-water for 15 minutes, fine crystals are obtained. After filtering and washing the crystals with ice-water, 18 g raw product is obtained. Mp 150°-170° C.

After recrystallization from water, 13 g of pure deutero 4,6-benzylidene-D-glucose, Mp 180°-182° C. is obtained.

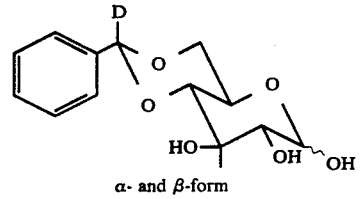

α- and β-form

The product was found to be pure on HPLC, and contains both the α and the β-anomers.

EXAMPLE 4

Method for preparing deutero 5,6-0-benzylidene ascorbic acid (and salts thereof).

40 g dry L-ascorbic acid was dissolved in 60 ml dry dimethylformamide and reacted with 41 g of deuterated α,α-dimethoxy-toluene (as prepared in Example 3) in the presence of 300 mg p-toluene sulfonic acid. The reaction mixture was held at 60° C. while continuously removing the formed methanol under reduced pressure. After the reaction had come to completion (all the calculated quantity of methanol has been removed), the DMF was distilled off under high vacuum.

The oily residue was stirred with ice-cold water to obtain white crystals of deuterated 5,6-0-benzylidene ascorbic acid.

The crystals can be further purified by recrystallization from benzene, but due to instability of the deutero 5,6-0-benzylidene ascorbic acid, it is recommended that the free acid be converted to the much more stable mono-basic salt by reacting the deutero 5,6-0-benzylidene-L-ascorbic acid with 13,5 g of sodium hydrogen carbonate in 300 ml water to obtain a clear solution of the mono-sodium salt of deutero 5,6-0-benzylidene-L-ascorbic acid. The structural formula is shown below. The structure has been confirmed by IR and NMR. The product is readily soluble in water. The pH of the solution is 6.6.

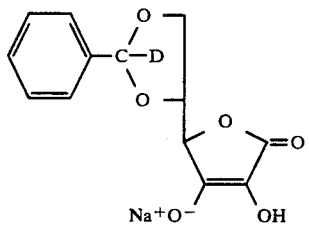

The beneficial properties of the drug composition according to the present invention are illustrated below in connection with a series of experiments which have been performed.

1) BIOLOGICAL MATERIALS AND METHODS USED TO DEMONSTRATE THE EFFECT

Cell Culturing Techniques and Synchronization

Human cells of the established line NHIK 3025, originating from a cervical carcinoma in situ (Nordbye, K., and Oftebro, R. Exp. Cell Res., 58: 458, 1969), Oftebro, R., and Nordbye, K., Exp. Cell Res., 58: 459–460, 1969) were cultivated in Medium E2a (Puck, T. T. et al., J. Exp. Med., 106: 155–165, 1957) supplemented with 20% human (prepared at the laboratory) and 10% horse serum (Grand Island Biological Co.). The cells are routinely grown as monolayers in tissue culture flasks. The cells do not move around after they have attached, a quality which enables us to observe the same cells in an inverted microscope for several cell generations.

The cells were kept in continuous exponential growth by frequent reculturing, i.e., every second and third day, and synchronized cell populations with a high degree of synchrony were obtained by repeated selection of mitotic cells (Pettersen, E. O. et al, Cell Tissue Kinet., 10: 511–522, 1977). During the synchronization procedure, the cells were kept in Medium E2a, and the whole experiment took place in a walk-in incubator at 37° C. Under growth conditions as used here, the NHIK 3025 cells have a medium cell-cycle time of ∼18 hr, with medium $G_1$, $S_1$ and $G_2$ durations of ∼7, ∼8, and ∼2.5 hr, respectively.

Cell Survival (Tables 1 and 7)

For measurement of cell survival, appropriate numbers of cells were seeded in plastic Petri dishes ($\phi=5$ cm). The number of cells seeded into each dish was adjusted such that the number of surviving cells would be approximately 150 per dish. While exponentially growing (asynchronous) cells were trypsinized before seeding, synchronized cells were seeded immediately after selection. After about 2 hr, the cells had attached to the bottom of the dishes, and the treatment was started by replacing the medium with medium containing the appropriate drug concentration. After the desired time of treatment, the drug-containing medium was removed, and fresh medium was added. The dishes were rinsed once with the same medium as was to be added on addition or removal of drug. After 10 to 12 days at 37° C. in a $CO_2$ incubator, the cells were fixed in ethanol and stained with methylene blue before the colonies were counted.

Duration of cell cycle-time (Table 3)

For detection of the drug effects on cell-cycle kinetics, the same methods were used as described previously (Lindmo, T., and Pettersen, E. O, Cell Tissue Kinet., 12: 43–57, 1979), (Pettersen, E. O. et al, Eur. J. Cancer Clin. Oncol., 19: 507–514; 1983), (Rønning, ø. W. et al., J. Cell. Physiol., 109: 411–419, 1981). Briefly, the selected mitotic cells were seeded into 8 tissue culture flasks (25 sq cm) 5000 cells per flask. The cells divided within 1 hr and attached as doublets to the bottom of the flasks. The cells within a delineated area of the flask ( 100 cells) were observed repeatedly in an inverted microscope, and the time of entrance into mitosis, as well as the time of division, were noted for each separate cell. Analyses of durations of mitosis were performed from these observations (Table 4).

Protein Synthesis (Tables 2, and 8)

The rate of protein synthesis was calculated as described previously (Rønning, ø. W. et al., J. Cell Physiol., 107: 47–57, 1981). Briefly, cellular protein was labeled to saturation during a 2-day preincubation with ($^{14}C$)valine of constant specific radioactivity (0.5 Ci/mol) prior to the experiment. This was achieved by using a high concentration of valine so that the dilution of ($^{14}C$)valine by intracellular valine and by proteolytically generated valine will be negligible (Rønning, ø. W., et al. Exp. Cell Res. 123: 63–72, 1979), thus keeping the specific radioactivity at a constant level. The rate of protein synthesis was calculated from the incorporation of ($^{3}H$)valine of constant specific activity. The incorporation measurements were related to the total of ($^{14}C$) radioactivity in protein at the beginning of the respective measurement periods and expressed as the percentage per hr (Rønning, ø. W. et al, J. Cell, Physiol. 107: 47–57, 1981).

Measurement of concentration of 4,6-0-benzylidene-D-glucose (BG) or 4,6-0-deuterobenzylidene-$d_1$-D-glucose (BG-$d_1$) in blood samples (Table 5)

Blood samples were taken from male Wistar rats immediately before and at several intervals after intravenous injection of BG or BG-$d_1$. Blood serum was separated by centrifugation. Equal amounts of blood serum and HPLC-grade acetonitrile were mixed and centrifuged at 13,000 rpm (15,000×g) for 5 minutes. Samples were then analyzed for BG or BG-$d_1$ content by High Performance Liquid Chromatography (HPLC). Samples were placed in an autosampler programmed for replicate injections of 20 1 each onto a 4.6×250 mm LC18 HPLC column. The column was eluted with 45% aqueous methanol delivered at 1 ml/min. BG or BG-$d_1$ were detected by using a spectrofluorometer set at excitation and emission wavelengths of 255 and 283 nm, respectively. The slit width used was 10 nm. Quantitation of the amount of BG or BG-$d_1$ in serum samples was performed with an electronic integrator calibrated with standard solutions of BG or BG-$d_1$ in the mobile phase (Pettersen et al., Anticancer Res., 6; 147-152, 1986).

Measurement of BG or BG-$d_1$ metabolites in blood samples (Table 6)

HPLC of blood samples was performed as indicated above. Relative amounts of BG- or BG-$d_1$-metabolite were determined by peak height analysis. The peak height from the electronic integrator (in microvolts) of samples taken 30 minutes after iv injection of BG, or 60 minutes after iv injection of BG-$d_1$ were normalized to 1. All other metabolite peaks were compared with these values.

Enkephalinase inhibiting activity of deuteroaldehydes and derivatives thereof

The enkephalinase inhibiting activity of deuteroaldehydes or derivatives of deuteroaldehydes was determined in vitro by assaying the ability of a purified enkephalinase-containing solution to hydrolyze (3H)-Leuenkephalin.

Specifically, aqueous solutions of deuteroaldehydes or deuteroaldehyde derivatives were added to an enkephalinase assay system and the activity of the enzymatic reaction decomposing enkephalin was determined. More specifically, the enzymatic activity of enkephalinase was measured as follows: 10 μl of 10 μCi (3H)-Leu-enkephalin, 20 μl of 2.5 mM Tris-HCl buffer and 30 μl of water were mixed and incubated at 37° C. for 5 minutes. Thereafter 30 μl of enkephalinase-containing solution was added and inbuation continued for 1 hour at 37° C. Finally 20 μl of 30% acetic acid was added and the reaction mixture was chromatographed using a Porapak Q column. The ratio of (3H)-Tyr-Cly-Gly to the original (3H)-Leu-enkephalin was determined using liquid scintillation counting.

The enkephalinase-inhibiting properties of deuteroaldehydes and deuteroaldehyde derivatives were determined by replacing the 30 μl added water in the above assay mixture with solutions containing aqueous solutions of deuteroaldehydes or deuteroaldehyde derivatives.

Concentration adjustments were made such that the final concentration of deuteroaldehyde or derivative of a deuteroaldehyde was between 1 and 1.5 mg/ml.

2) BIOLOGICAL EFFECTS

The cytotoxic effect of benzaldehyde and of deuterobenzaldehyde-$d_1$ was tested on asynchronous, exponentially growing NHIK 3025 cells by counting the number of cells able to form colonies after 24 hr treatment in Petri dishes. In Table 1 the results represent 2 different, independent experiments where the numbers give the mean fraction of surviving cells from 10 parallel dishes (± standard error).

TABLE 1

Fraction of cells surviving 24 hr treatment with benzaldehyde or deuterobenzaldehyde-$d_1$ in Petri dishes. (The values represent the mean ± standard error from 10 different dishes.)

| Drug | Drug concentration (mM) | |
|---|---|---|
| | 3.2 | 12.8 |
| Benzaldehyde | 0.64 ± 0.18 | 0.024 ± 0.0080 |
| Deuterobenzaldehyde-$d_1$ | 0.68 ± 0.14 | 0.0056 ± 0.0020 |

Conclusion: With the highest concentration of drugs there is a significantly stronger cell inactivation with deuterobenzaldehyde-$d_1$ than with benzaldehyde.

Benzaldehyde has been shown to inhibit protein synthesis in a reversible manner, i.e. during treatment the protein synthesis is below normal, but constant as long as the treatment lasts. After treatment protein synthesis increases back to normal over a time period of 1 to 2 hr (Pettersen et al., Eur. J. Cancer Clin. Oncol. 19: 935-940, 1983).

Table 2 shows the protein synthesis of cells treated for a 4 hr period with benzaldehyde as well as with deuterobenzaldehyde-$d_1$.

The incorporation of ($^3$H)-valine was measured either during the 1st hr after the start of treatment or during the 1st or 2nd hr after the termination of treatment (pulse 4-5) or (pulse 5-6). The last measurements were done to test the reversibility of the drugs. Drug concentration: 3.2 mM.

TABLE 2

Protein synthesis inhibition by benzaldehyde and deuterobenzaldehyde-$d_1$. (The values represent the mean ± standard error from 4 different measurements.)

| Drug | Pulse | | Protein synthesis %/hr |
|---|---|---|---|
| Control | | | 6.8 ± 0.9 |
| Benzaldehyde | 0-1 | During treatment | 3.7 ± 0.3 |
| Deuterobenzaldehyde-$d_1$ | 0-1 | | 3.6 ± 0.3 |
| Benzaldehyde | 4-5 | After treatment | 5.1 ± 0.3 |
| Deuterobenzaldehyde-$d_1$ | 4-5 | | 4.7 ± 0.3 |
| Benzaldehyde | 5-5 | | 6.7 ± 0.5 |
| Deuterobenzaldehyde-$d_1$ | 5-6 | | 5.8 ± 0.3 |

Conclusion: During this treatment the protein synthesis inhibition is the same. Deuterobenzaldhyde-$d_1$ is somewhat less reversible than benzaldehyde, although this effect is weak.

Cell Cycle Inhibition

Benzaldehyde inhibits cell cycle progression as a secondary effect of the inhibiton of protein synthesis (Petterson et al. Eur. J. Cancer Clin. Oncol. 19: 507-514, 1983 and 19: 935-940, 1982). Since the deutero-compound seems to be less reversible on protein synthesis inhibition than the undeuterated compound, we therefore expected it to also induce a more pronounced increase in cell-cycle duration than the undeuterated one after pulse-treatment. This is shown by the data in Table 3, where we have used synchronized cells treated over an 8 hr period starting 2 hr after mitotic selection, i.e. when the cells were in early G1.

TABLE 3

Cell cycle inhibition of synchronized cells treated for 8 hr with benzaldehyde or deuterobenzaldehyde-$d_1$.

| Drug | Concentration (mM) | Duration of the part of the cell cycle starting 2 hr after selection | Prolongation % |
|---|---|---|---|
| Control 1 | | 16.5 | |
| Banzaldehyde | 2 | 17.8 | 7.9 |
| Deutero-benzaldehyde-$d_1$ | 2 | 19.0 | 15.2 |
| Control 2 | | 16.8 | |
| Benzaldehyde | 2.5 | 27.5 | 63.7 |
| Deutero-benzaldehyde-$d_1$ | 2.5 | 35.0 | 108.3 |

Conclusion: Deuterobenzaldehyde-$d_1$ clearly induces a more extensive increase in cell-cycle duration than benzaldehyde. The difference may result from differences in reversibility of protein synthesis inhibition. Thus, even for deuterobenzaldehyde the cell-cycle inhibition may very well be a secondary result of the protein synthesis inhibition.

Benzaldehyde induces specific inhibition during mitosis (Pettersen et al., Eur. J. Cancer, Clin, Oncol. 19: 507-514, 1983). This effect is probably directly related to the aldehyde group (Pettersen et al. Cancer Res. 45: 1085-2091, 1985). If the deuterated aldehyde group induces different biological effects from the undeuterated one it is therefore good reason to expect this to be expresses as a difference in effect on cells in mitosis. In Table 4 results are shown on prolongation of mitosis of snychronized cells treated with benzaldehyde or deuterobenzaldehyde-$d_1$ during mitosis. The numbers in the table represent the percentage of the cells having a duration of mitosis below 1 hr (which is normal for untreated cells) or above the number of hours indicated on top of each column.

TABLE 4

Duration of mitosis for untreated cells and for cells treated with benzaldehyde or deuterobenzaldehyde-$d_1$ (3.2 mM) during mitosis.

| Drug | <1 | >1 | >2 | >3 | >4 | >5 | >6 |
|---|---|---|---|---|---|---|---|
| Control | 83% | 17% | 4% | 2% | | | |
| Benzaldehyde | 5% | 95% | 87% | 70% | 49% | 35% | 21% |
| Deutero-benzaldehyde-$d_1$ | 13% | 87% | 81% | 74% | 70% | 69% | 64% |

Conclusion: Deuterobenzaldehyde-$d_1$ is clearly more efficient as a mitotic inhibitor than benzaldehyde.

Benzaldehyde is a compound which has a strongly irritating effect on mucous membranes, and cannot be given to animals or patients in its pure form. It is therefore important that non-irritating derivatives can be synthesized which have retained the cytotoxic and the protein-synthesis inhibiting effects of benzaldehyde. One such compound is 4,6-0-benzylidine-D-glucose (BG) which has been tested on tumour-bearing animals (Pettersen et al. Anticancer Res. 6: 147-152, 1986) as well as on patients (Kochi et al., Cancer Treat. Rep. 69: 533-537, 1985). While BG has a relatively short half-life in vivo, we have found that a metabolite is formed which has a somewhat longer half-life. This metabolite may possess an anticancer effect.

We have compared the metabolism in rats of BG as well as of deuterated BG (BG-$d_1$) In Table 5 the serum concentration of BG or BG-$d_1$ is shown at various time points after a single iv injection of each drug, respectively.

TABLE 5

The amounts (mM) of unmetalbolized BG or BG-$d_1$ in blood samples as a function of time after iv injection.

| Minutes after iv injection | BG mM | BG-$d_1$ mM |
|---|---|---|
| 0 | 0.345 (estimated) | 0.345 (estimated) |
| 2 | 0.23 ± 0.016 | 0.22 ± 0.02 |
| 5 | 0.11 ± 0.010 | 0.16 ± 0.02 |
| 10 | 0.096 ± 0.015 | 0.14 ± 0.02 |
| 15 | 0.066 ± 0.018 | 0.10 ± 0.02 |
| 20 | 0.048 ± 0.011 | 0.097 ± 0.003 |
| 25 | 0.040 ± 0.005 | N.D. |
| 30 | 0.033 ± 0.008 | 0.066 ± 0.015 |
| 60 | N.F. | 0.010 ± 0.005 |

N.D. = Not Determined,
N.F. = Not Found

Each value represents the average of two to five independent measurements ±S.E.

Conclusion: These results indicate that BG is metabolized in vivo with a half-life on the order of 5 minutes. The half-life measured following injection with BG-$d_1$, however, was approximately 15 minutes. Therefore the initial metabolism of BG-$d_1$ is slower than that of the undeuterated compound.

At the same time as BG or BG-$d_1$ metabolism was being determined, a separate metabolite peak appeared in HPLC chromatograms. The increase in BG- and BG-$d_1$-metabolite and subsequent clearance was measured.

TABLE 6

The relative amount of metobolite as a function of the time after iv injection of BG or BG-$d_1$.

| Minutes after iv injection | BG Metabolite | BG-$d_1$ Metabolite |
|---|---|---|
| 2 | 0.365 ± 0.010 | 0.360 ± 0.010 |
| 5 | 0.422 ± 0.062 | 0.717 ± 0.032 |
| 10 | 0.730 ± 0.025 | 0.725 ± 0.055 |
| 15 | 0.878 ± 0.032 | 0.855 ± 0.044 |
| 20 | 0.837 ± 0.013 | 0.820 ± 0.010 |
| 25 | 0.952 ± 0.042 | N.D. |
| 30 | 1.00 | 0.945 ± 0.026 |
| 45 | 0.927 ± 0.008 | 0.995 ± 0.008 |
| 60 | 0.650 ± 0.046 | 1.00 |
| 90 | 0.480 ± 0.007 | 0.797 ± 0.049 |
| 120 | 0.320 ± 0.045 | 0.677 ± 0.088 |

N.D. = Not Determined

Each value represents the average of two to five independent measurements, ±S.E.

Conclusion: Two conclusions can be reached from these data. Firstly, the formation of metabolite from BG is faster than from BG-$d_1$. The peak height of BG-metabolite reaches a maximum (=1) at 30 minutes after iv injection while BG-$d_1$-metabolite reaches a maximum after 60 minutes. Secondly, clearance (or further metabolization) is much more rapid for BG than BG-$d_1$. The relative amount of BG metabolite 120 minutes after iv injection of BG-$d_1$ was the same as the relative amount of metabolite originating from BG at 60 minutes after i.v.

The metabolism of BG which takes place in vivo is not seen in vitro, where the compound is stable over a period of at least 24 hr. It is therefore relevant to compare both the cytotoxic and the protein synthesis inhibitory effects of BG and BG-$d_1$ on cells in vitro. These results are shown in Table 7 and in Tables 8 and 9, respectively.

TABLE 7

Cell survival of cells treated for 24 hr with BG or BG-$d_1$.

| Drug | Drug concentration (mM) | |
|---|---|---|
|  | 6.4 | 12.8 |
| BG | 0.30 ± 0.05 | 0.0078 ± 0.0018 |
| BG-$d_1$ | 0.33 ± 0.07 | 0.0080 ± 0.0030 |

TABLE 8

Protein synthesis inhibition by 4,6-O-benzylidene-D-glucose (BG) and 4,6-O-deuterobenzylidene-$d_1$-D-glucose (BG-$d_1$).

| Drug | Concentration (mM) | Pulse (hr) | | Protein synthesis (%/hr) |
|---|---|---|---|---|
| 1. Asynchronous cells, short treatment of 3 hr (2 dishes, 4 measurements of each group.) | | | | |
| Control | | | | 5.7 ± 0.5 |
| BG | 3.2 | 0–1 | During treatment | 2.9 ± 0.7 |
| BG-$d_1$ | 3.2 | 0–1 | | 3.0 ± 0.3 |
| BG | 3.2 | 2–3 | | 2.9 ± 0.1 |
| BG-$d_1$ | 3.2 | 2–3 | | 3.4 ± 0.3 |
| 2. Synchronized cells, long time treatment of 22 hr. Reversibility test (2 dishes, measurements of each group.) | | | | |
| Control | | | | 5.3 ± 0.2 |
| BG | 3.2 | 21–22 | During treatment | 4.8 ± 0.5 |
| BG-$d_1$ | 3.2 | 21–22 | | 4.6 ± 0.2 |
| BG | 3.2 | 23–24 | After treatment | 5.5 ± 0.1 |
| BG-$d_1$ | 3.2 | 23–24 | | 5.4 ± 0.1 |

Conclusion: Tables 7 and 8 show that unmetabolized BG and BG-$d_1$ have similar effect on cell survival as well as on protein synthesis.

The deuteroaldehydes of the present invention may be formulated into pharmaceutical compositions by numerous ways.

The primary utility for the compounds included in this invention, namely deuteroaldehydes and derivatives thereof, is as active ingredients of anticancer drug compositions. These anticancer drug compositions containing an active ingredient compound may be administered orally or parenterally. For oral administration the anticancer drug composition may be given in the form of tablets, capsules, granules or powders. For parenteral administration the anticancer composition may be given in a form suitable for injection, intravenous infusion or suppository.

The active deuteroaldehyde or deuteroaldehyde derivative may be formulated into an anticancer composition by association with a pharmaceutically acceptable carrier, either solid or liquid. Deuteroaldehydes may specifically be formulated into anticancer compositions by forming inclusion compounds with, for example, β-cyclodextrin. In making anticancer compositions containing deuteroaldehydes or derivatives thereof, surfactants, vehicles, lubricants, adjuvants and pharmacologically acceptable film-forming materials may be used as is known in the pharmaceutical art.

The proportion of active ingredient deuteroaldehyde or deuteroaldehyde derivative in the anticancer composition will vary depending upon the type of preparation but may generally be within the range of approximately 0.1 to 20% by weight for oral administration and for absorption through mucous membranes, and about 0.01 to 10% by weight for parenteral administration.

Suitable ranges for the dosage of the active component of pharmaceutical anticancer compositions will be in the range of 0.5 to 1.5 g/sq.m.

However, the dosage will be dependent upon the curing effect and the period of time to elicit a cure.

Treatment of human cancer diseases by anticancer compositions containing as the active ingredient deuteroaldehydes or derivatives thereof may be indicated by, although not limited to, carcinomas of the brain, head and neck, lung, tongue, gastrointestinal tract, colon and rectum; and metastases of the above.

Previous knowledge indicates that some aldehydes and aldehyde derivatives possess pain alleviating properties apparently resulting from the inhibition of the enzyme enkephalinase.

Deuteroaldehydes and derivatives thereof may, as a second utility, be used as the active ingredients of pharmaceutical compositions for alleviating pain, i.e. analgesic compositions. These compositions contain, as the active ingredient a deuteroaldehyde with a stabilizing amount of cyclodextrin, or a suitable amount of a deuteroaldehyde-sugar acetal derivative combined with a pharmaceutically acceptable carrier. The compositions may be in the form of tablets, capsules, granules, powder or other form suitable for oral administration. These compositions are prepared by conventional procedures.

Compositions administered intravenously, by infusion, or rectally are also prepared by conventional procedures known in the pharmaceutical art.

Preferably deuteroaldehydes are administered orally as cyclodextrin inclusion compounds while sugar-acetal derivatives of deuteroaldehydes are preferably administered intravenously.

A wide dosage range may be administered depending on the severity of the pain experienced. Deuteroaldehydes and deuteroaldehyde derivatives may be administered as the sole analgesic agent or may be administered in combination with one or more additional analgesic agents.

Indications for use include, but are not limited to, treating pain due to various cancerous diseases, peptic and duodenal ulcers, etc., and pain resulting from the administration of various drugs.

The amount of deuteroaldehyde and deuteroaldehyde derivatives to be administered would depend on the medical history of the patient, the severity of the pain experienced, and the cause thereof. Generally from about 0.1 to 2.5 g from one to four times per day would be the dosage range for an average human adult.

More specifically, a useful dose range is about 500 mg per day administered in four doses of approximately 125 mg per dose.

Technical and Biological Effects

The present invention involves deuteroaldehydes and derivatives thereof. The improved in vitro and in vivo biological effect of these compounds may be due to a kinetic deuterium isotope effect, also termed the kinetic isotope effect. This effect explains the slower reaction kinetics of compounds containing deuterium than for compounds containing hydrogen since a bond to deuterium is broken slower than a bond to hydrogen. Another effect, the secondary kinetic isotope effect, may also affect formation of carbonium ions. Thus, two isotope effects may be responsible for the improvement in biological activity represented by the present compounds.

From our previous studies benzaldehyde has been shown to induce, as a primary effect, a protein synthesis inhibition. As a secondary consequence of this primary effect cell-cycle progression is reduced during benzaldehyde treatment and furthermore, for long treatment times and high drug doses, there is a cell inactivation. Another effect of benzaldehyde is a specific prolongation of mitosis. Of these two effects (protein synthesis inhibition and mitotic inhibition), only protein synthesis inhibition is known to appear during treatment with BG which does not have a free aldehyde group. Thus, a tempting speculation is that the aromatic ring, on the one hand, which is the common structure in the two compounds, is of great functional importance with respect to protein synthesis inhibition while it is of less importance with respect to mitotic inhibition. The aldehyde group, on the other hand, could be vital with respect to mitotic inhibition, but not necessarily with respect to protein synthesis inhibition. The inactivating effect of both benzaldehyde and BG is probably a result, mainly, of the protein synthesis inhibition. The exception is cells treated during mitosis, which are inactivated efficiently by benzaldehyde, but not by BG.

More specifically, the duration of mitosis of human cells treated in culture was significantly more increased by treatment with deuterobenzaldehyde-$d_1$ as compared to treatment with benzaldehyde. The stability and longevity of a reaction product formed from deuterobenzaldehyde-$d_1$ as compared to benzaldehyde may be responsible for the observed mitotic inhibitory properties of deuterobenzaldehyde-$d_1$.

Protein synthesis inhibition induced by benzaldehyde may be due to interactions involving the aromatic ring moiety and not specifically the aldehyde group. Since both benzaldehyde and deuterobenzaldehyde-$d_1$ induced relatively equivalent inhibition of protein synthesis, and BG and BG-$d_1$ also induced similar results, the introduction of deuterium into these compounds did not increase their specific effects on protein synthesis. However, recovery from protein synthesis inhibition was measurably slower when cells were pulse-treated with deuterobenzaldehyde-$d_1$ than with benzaldehyde. Thus cells would still be exposed to some deuterobenzaldehyde-$d_1$ even after the medium containing this compound was removed.

As mentioned above, the expected consequence of deuteration is that incorporation of deuterium into a compound would cause greater stability of chemical deuterium bonds than to hydrogen. The in vivo experiments utilizing BG and BG-$d_1$ appear to confirm this belief. A clearly slower metabolism and clearance from serum of BG-$d_1$ as compared to BG when injected into rats was found. BG and BG-$d_1$ metabolism may be dependent upon hydrolysis of the acetal linkage between the aromatic moiety and sugar moiety of the molecule. It was shown that a metabolite of BG or BG-$d_1$ was formed in vivo, and that the metabolite formed from BG-$d_1$ exhibited slower clearance kinetics than that formed from BG. The prolonged presence in blood is of major clinical importance, and could also reduce the need for frequent iv administration. In this way an improved biological effect was obtained by these new deutero compounds.

The present invention thus makes use of deuteroaldehydes and derivatives thereof in the formulation of anticancer drug compositions, the use of which will yield a greater thereapeutic effect for cancer patients than established conventional chemotherapy.

We claim:

1. A compound selected from the group consisting of a compound of the formula:

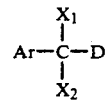

wherein Ar is phenyl substituted by alkyl of 1-5 carbon atoms, cycloalkyl of 3-6 carbon atoms, halogen, nitro, amino, monoalkylamino of 1-5 carbon atoms or dialkylamino of 1-5 carbon atoms in each alkyl group, or is unsubstituted phenyl, which substituted or unsubstituted phenyl is non-deuterated or partly or completely deuterated, and $X_1$ and $X_2$ together with the carbon atom to which they are attached form a cyclic thioacetal, dithiane or oxazolidine, and a pharmaceutically acceptable salt thereof, with the proviso that when Ar is unsubstituted phenyl, then $X_1$ and $X_2$ cannot be dithiane.

* * * * *